United States Patent
Zhang et al.

(10) Patent No.: US 8,633,217 B2
(45) Date of Patent: Jan. 21, 2014

(54) CRYSTAL FORMS OF KINASE INHIBITORS

(75) Inventors: Geoff G. Z. Zhang, Vernon Hills, IL (US); Douglas H. Hoffman, Libertyville, IL (US); Jonathan Miller, Lindenhurst, IL (US)

(73) Assignee: AbbVie Inc., North Chicago, IL (US)

( * ) Notice: Subject to any disclaimer, the term of this patent is extended or adjusted under 35 U.S.C. 154(b) by 205 days.

(21) Appl. No.: 13/155,534

(22) Filed: Jun. 8, 2011

(65) Prior Publication Data
US 2012/0202844 A1 Aug. 9, 2012

Related U.S. Application Data

(60) Provisional application No. 61/353,038, filed on Jun. 9, 2010.

(51) Int. Cl.
*A01N 43/42* (2006.01)
*A61K 31/44* (2006.01)
*C07D 513/02* (2006.01)
*C07D 515/02* (2006.01)

(52) U.S. Cl.
USPC .................................. 514/301; 546/114

(58) Field of Classification Search
USPC .......................... 514/301; 546/114
See application file for complete search history.

(56) References Cited

U.S. PATENT DOCUMENTS

2005/0043347 A1* 2/2005 Betschmann et al. ........ 514/301
2010/0144783 A1 6/2010 Michaelides

FOREIGN PATENT DOCUMENTS

WO WO2010065825 A2 6/2010

OTHER PUBLICATIONS

Gould, International Journal of Pharmaceutics, 1986, Elsevier, vol. 33, Nos. 1-3, pp. 201-217.*
Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.
Tse, C. et al., "ABT-263: A Potent and Orally Bioavailable Bcl-2 Family Inhibitor," Cancer Research, 2008, vol. 68 (9), pp. 3421-3428—Including Supplementary Data.
International Search Report and Written Opinion for Application No. PCT/US2011/039582, mailed on Sep. 30, 2011, 10 pages.
International Search Report and Written Opinion for Application No. PCT/US2011/039591, mailed on Sep. 30, 2011, 10 pages.
International Search Report and Written Opinion for Application No. PCT/US2011/039603, mailed on Sep. 28, 2011, 10 pages.

* cited by examiner

*Primary Examiner* — Sarah Pihonak
(74) *Attorney, Agent, or Firm* — Susan L. Steele

(57) ABSTRACT

Citrate salts of N-(4-{4-amino-7-[1-(2-hydroxyethyl)-1H-pyrazol-4-yl]thieno[3,2-c]pyridin-3-yl}phenyl)-N'-(3-fluorophenyl)urea and crystalline forms thereof are suitable pharmaceutical ingredients for pharmaceutical compositions useful in the treatment of disease, for example, cancer.

7 Claims, 2 Drawing Sheets

CRYSTAL FORMS OF KINASE INHIBITORS

CROSS-REFERENCE TO RELATED APPLICATIONS

This application claims priority to U.S. Provisional Application Ser. No. 61/353,038 filed Jun. 9, 2010, which is incorporated by reference in its entirety.

FIELD OF THE INVENTION

The present invention relates to crystalline forms of citrate salts of N-(4-{4-amino-7-[1-(2-hydroxyethyl)-1H-pyrazol-4-yl]thieno[3,2-c]pyridin-3-yl}phenyl)-N'-(3-fluorophenyl) urea, processes for preparing the crystalline forms, pharmaceutical formulations thereof, and methods of treating cancer.

BACKGROUND OF THE INVENTION

Mitosis is a process by which a complete copy of a duplicated genome is segregated by the microtuble spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

The reversible phosphorylation of proteins is one of the primary biochemical mechanisms mediating eukaryotic cell signaling. This reaction is catalyzed by protein kinases that transfer the g-phosphate group of ATP to hydroxyl groups on target proteins. 518 such enzymes exist in the human genome of which ~90 selectively catalyze the phosphorylation of tyrosine hydroxyl groups. Cytosolic tyrosine kinases reside intracellularly whereas receptor tyrosine kinases (RTKs) possess both extracellular and intracellular domains and function as membrane spanning cell surface receptors. As such, RTKs mediate the cellular responses to environmental signals and facilitate a broad range of cellular processes including proliferation, migration and survival.

RTK signaling pathways are normally highly regulated, yet their over-activation has been shown to promote the growth, survival and metastasis of cancer cells. Dysregulated RTK signaling occurs through gene over-expression or mutation and has been correlated with the progression of various human cancers.

The VEGF receptor (VEGFR) family consists of three RTKs, KDR (kinase insert domain-containing receptor; VEGFR2), FLT1 (Fms-like tyrosine kinase; VEGFR1), and FLT4 (VEGFR3). These receptors mediate the biological function of the vascular endothelial growth factors (VEGF-A, -B, -C, -D, -E and placenta growth factor (PlGF)), a family of homodimeric glycoproteins that bind the VEGF receptors with varying affinities.

KDR is the major mediator of the mitogenic, angiogenic and permeability-enhancing effects of VEGF-A, hereafter referred to as VEGF. Many different cell types are able to produce VEGF, yet its biological activity is limited predominately to the vasculature by way of the endothelial cell-selective expression of KDR. Not surprisingly, the VEGF/KDR axis is a primary mediator of angiogenesis, the means by which new blood vessels are formed from preexisting vessels.

FLT1 binds VEGF, VEGF-B and placental growth factor. FLT1 is expressed on the surface of smooth muscle cells, monocytes and hematopoietic stems cells in addition to endothelial cells. Activation of FLT1 signaling results in the mobilization of marrow-derived endothelial progenitor cells that are recruited to tumors where they contribute to new blood vessel formation.

FLT4 mediates the signaling of VEGF-C and VEGF-D, which mediate formation of tumor-associated lymphatic vessels (lymphangiogenesis). Lymphatic vessels are one of the routes by which cancer cells disseminate from solid tumors during metastasis.

The PDGF receptor (PDGFR) family consists of five RTK's, PDGFR-a and -b, CSF1R, KIT, and FLT3.

CSF-1R is encoded by the cellular homolog of the retroviral oncogene v-fms and is a major regulator of macrophage development. Macrophages are frequent components of tumor stroma and have been shown to modify the extracellular matrix in a manner beneficial to tumor growth and metastasis.

KIT is expressed by hematopoietic progenitor cells, mast cells, germ cells and by pacemaker cells in the gut (interstitial cells of Cajal). It contributes to tumor progression by two general mechanisms namely autocrine stimulation by its ligand, stem cell factor (SCF), and through mutations that result in ligand-independent kinase activity.

FLT3 is normally expressed on hematopoietic stem cells where its interaction with FLT3 ligand (FL) stimulates stem cell survival, proliferation and differentiation. In addition to being over-expressed in various leukemia cells, FLT3 is frequently mutated in hematological malignancies with approximately one-third of patients with acute myeloid leukemia (AML) harboring activating mutations.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

Compounds that inhibit protein kinases such as Aurora-kinases and the VEGFR and PDGFR families of kinases have been identified, including N-(4-{4-amino-7-[1-(2-hydroxyethyl)-1H-pyrazol-4-yl]thieno[3,2-c]pyridin-3-yl}phenyl)-N'-(3-fluorophenyl)urea. These compounds, and methods to make them, are disclosed in U.S. patent application Ser. No. 12/632,183 (hereinafter "the '183 application"), incorporated by reference herein in its entirety.

It now has been found that citrate salts of N-(4-{4-amino-7-[1-(2-hydroxyethyl)-1H-pyrazol-4-yl]thieno[3,2-c]pyridin-3-yl}phenyl)-N'-(3-fluorophenyl)urea can be converted into crystalline forms, which can advantageously be used as an active pharmaceutical ingredient in cancer therapy. To that purpose, these crystalline forms are converted into pharmaceutical formulations.

A crystalline form is the form in which the position of the molecules relative to one another is organized according to a three-dimensional lattice structure. Polymorphs are different crystalline forms of the same compound resulting from a different arrangement of the molecules in the solid state. Polymorphs differ from each other in their physical properties but not their chemical composition.

Polymorphism is of particular interest in the development of suitable pharmaceutical dosage forms. Certain polymorphic forms may exhibit superior stability and storability, resulting in enhanced shelf-life of the pharmaceutical product. In addition, certain polymorphic forms are more readily manufactured in high purity in large quantities.

Critically, polymorphs of an active pharmaceutical ingredient can have different aqueous solubility and dissolution rates, which may have therapeutic consequences due to the potential differences in bioavailability between polymorphs of the same compound.

The present invention provides crystalline forms of citrate salts of N-(4-{4-amino-7-[1-(2-hydroxyethyl)-1H-pyrazol-4-yl]thieno[3,2-c]pyridin-3-yl}phenyl)-N'-(3-fluorophenyl) urea having beneficial properties in one or more of the following characteristics: the ability to be formulated in a pharmaceutical dosage form, adequate shelf-life in a pharmaceutical dosage form, and/or ability to be effectively administered in a pharmaceutical dosage form.

SUMMARY OF THE INVENTION

In one embodiment, the invention provides N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in solid crystalline form.

In one embodiment, the invention provides N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate in solid crystalline form.

In a further embodiment, the invention provides a crystal polymorph of N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate characterized herein and designated dihydrogen citrate Form I.

In a further embodiment, the invention provides hydrated forms of dihydrogen citrate Form I, including the monohydrate form.

In a further embodiment, the invention provides a crystal polymorph of N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate characterized herein and designated hydrogen citrate Form II.

In a further embodiment, the invention provides hydrated forms of hydrogen citrate Form II, including the monohydrate form.

There is further provided a pharmaceutical composition comprising N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I and one or more pharmaceutically acceptable excipients.

There is further provided a pharmaceutical composition comprising N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate Form II and one or more pharmaceutically acceptable excipients.

There is further provided process for preparing N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I comprising providing a mixture comprising N-(4-{4-amino-7-[1-(2-hydroxyethyl)-1H-pyrazol-4-yl]thieno[3,2-c]pyridin-3-yl}phenyl)-N'-(3-fluorophenyl)urea, water, acetone, and citric acid, and causing the N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I to exist in the mixture.

There is further provided process for preparing N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate Form II comprising providing a mixture comprising N-(4-{4-amino-7-[1-(2-hydroxyethyl)-1H-pyrazol-4-yl]thieno[3,2-c]pyridin-3-yl}phenyl)-N'-(3-fluorophenyl)urea, water, tetrahydrofuran, and citric acid, and causing the N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate Form II to exist in the mixture.

In a further embodiment, the invention provides a method for treating cancer in a mammal comprising administering to a subject having the disease therapeutically effective amount of citrate salts of N-(4-{4-amino-7-[1-(2-hydroxyethyl)-1H-pyrazol-4-yl]thieno[3,2-c]pyridin-3-yl}phenyl)-N'-(3-fluorophenyl)urea in a solid crystalline form, wherein the crystalline form is Form I or II, or (b) a pharmaceutical composition comprising citrate salts of N-(4-{4-amino-7-[1-(2-hydroxyethyl)-1H-pyrazol-4-yl]thieno[3,2-c]pyridin-3-yl}phenyl)-N'-(3-fluorophenyl)urea in a solid crystalline form, wherein the crystalline form is Form I or II, one or more pharmaceutically acceptable excipients. Examples of such cancers include myelodysplastic syndrome, acute myeloid leukemia, colorectal cancer, non-small cell lung cancer, and ovarian cancer.

There is still further provided a method for treating cancer in a mammal comprising dissolving N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form, wherein the crystalline form is Form I, in a pharmaceutically acceptable solvent or mixture of solvents, and administering the resulting solution in a therapeutically effective amount to subject having the disease.

There is still further provided a method for treating cancer in a mammal comprising dissolving N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form, wherein the crystalline form is Form I, in a pharmaceutically acceptable solvent or mixture of solvents, and administering the resulting solution in a therapeutically effective amount to subject having the disease.

There is still further provided a method for treating cancer in a mammal comprising dispersing N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate in a solid crystalline form, wherein the crystalline form is Form II, in a pharmaceutically acceptable polymeric carrier, and administering the resulting solid dispersion in a therapeutically effective amount to subject having the disease.

There is still further provided a method for treating cancer in a mammal comprising dissolving N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate in a solid crystalline form, wherein the crystalline form is Form II, in a pharmaceutically acceptable solvent or mixture of solvents, and administering the resulting solution in a therapeutically effective amount to subject having the disease.

Additional embodiments of the invention, including more particular aspects of those provided above, will be found in, or will be evident from, the detailed description that follows.

DETAILED DESCRIPTION

Figure 1:
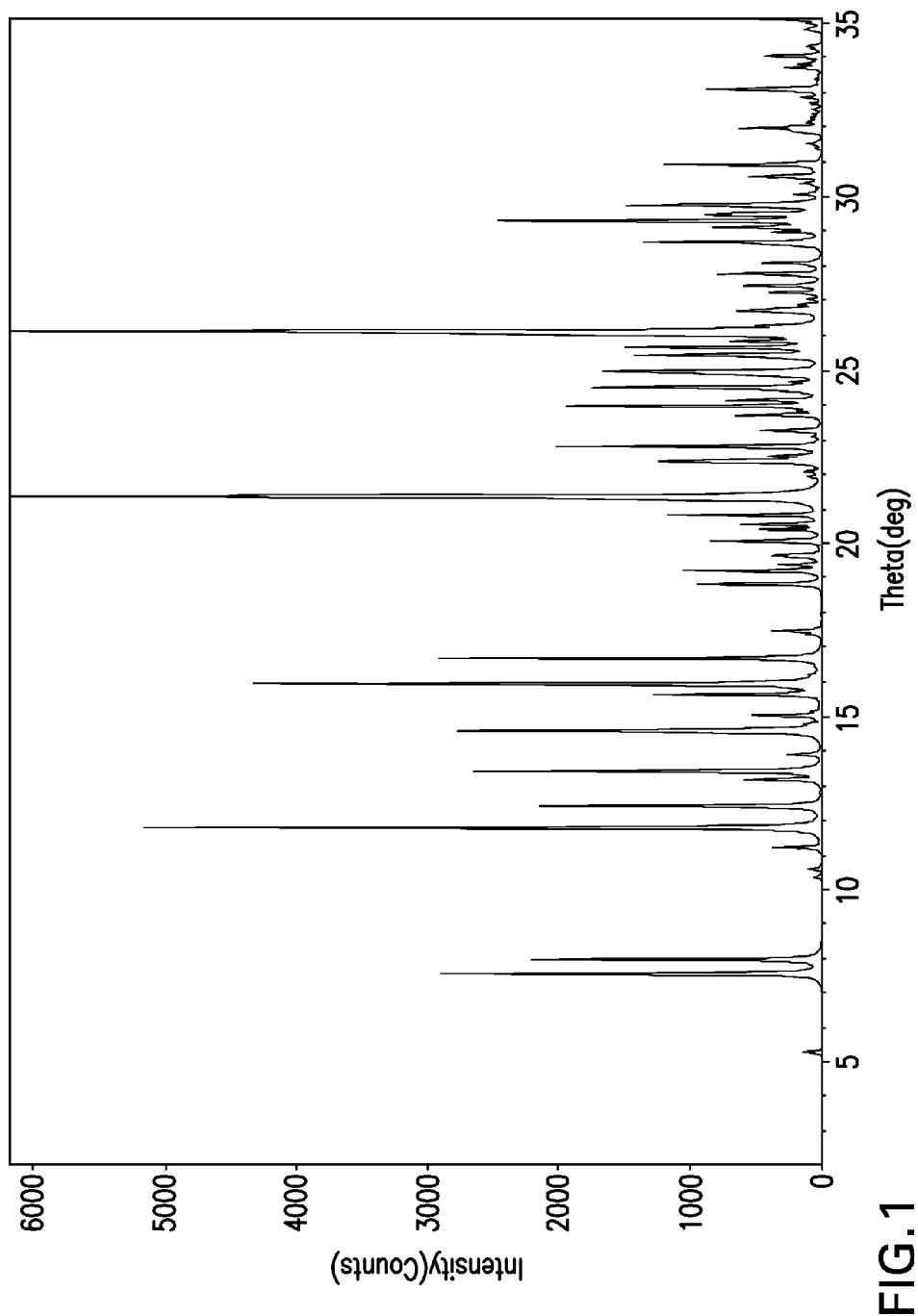
FIG. 1 is a PXRD scan of crystal polymorph Form I N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate.
Figure 2:
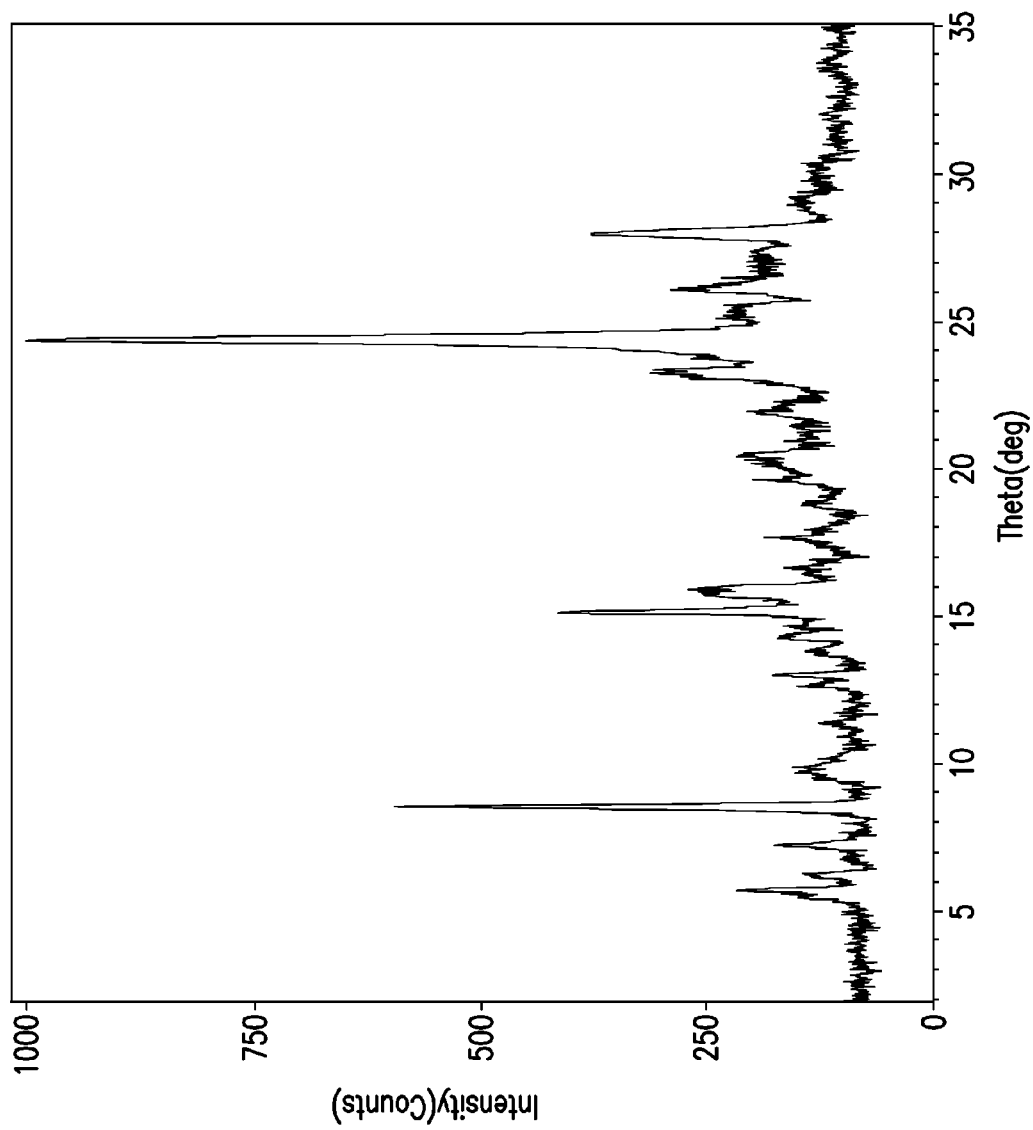
FIG. 2 is a PXRD scan of crystal polymorph Form II N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate.

The invention encompasses crystalline forms of citrate salts of N-(4-{4-amino-7-[1-(2-hydroxyethyl)-1H-pyrazol-4-yl]thieno[3,2-c]pyridin-3-yl}phenyl)-N'-(3-fluorophenyl) urea. N-(4-{4-amino-7-[1-(2-hydroxyethyl)-1H-pyrazol-4-yl]thieno[3,2-c]pyridin-3-yl}phenyl)-N'-(3-fluorophenyl) urea free base is prepared, illustratively, as described in Example 1 of above-cited U.S. patent application Ser. No. 12/632,183, the entire disclosure of which is incorporated by reference herein. The term "free base" is used for convenience herein to refer to N-(4-{4-amino-7-[1-(2-hydroxyethyl)-1H-pyrazol-4-yl]thieno[3,2-c]pyridin-3-yl}phenyl)-N'-(3-fluorophenyl)urea parent compound as distinct from any salt thereof.

Those skilled in the art will also understand that the term "monohydrate" when referring to N-(4-{4-amino-7-[1-(2-hydroxyethyl)-1H-pyrazol-4-yl]thieno[3,2-c]pyridin-3-yl}phenyl)-N'-(3-fluorophenyl)urea means that there is one water molecule for every molecule of N-(4-{4-amino-7-[1-(2-hydroxyethyl)-1H-pyrazol-4-yl]thieno[3,2-c]pyridin-3-yl}phenyl)-N'-(3-fluorophenyl)urea.

In one embodiment, the invention encompasses N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form.

In one embodiment the invention encompasses a crystalline form of N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate, characterized at least by a powder X-ray diffraction peak at any one or more of the following positions: 11.80, 14.59, 15.95, 21.38, 26.12° 2θ, ±0.2° 2θ, herein defined as Form I.

Another aspect of the invention encompasses a crystalline form of N-(4-{4-amino-7-[1-(2-hydroxyethyl)-1H-pyrazol-4-yl]thieno[3,2-c]pyridin-3-yl}phenyl)-N'-(3-fluorophenyl) urea dihydrogen citrate Form I, characterized at least by a powder X-ray diffraction peak at each of the following positions: 11.80, 14.59, 15.95, 21.38, 26.12° 2θ, ±0.2° 2θ.

Another aspect of the invention encompasses a crystalline form of N-(4-{4-amino-7-[1-(2-hydroxyethyl)-1H-pyrazol-4-yl]thieno[3,2-c]pyridin-3-yl}phenyl)-N'-(3-fluorophenyl) urea dihydrogen citrate Form I, characterized at least by a powder X-ray diffraction peak at each of the following positions: 7.56, 7.96, 11.80, 12.42, 13.44, 14.59, 15.66, 15.95, 16.69, 21.38, 22.40, 22.82, 23.98, 24.50, 24.99, 26.12° 2θ, ±0.2° 2θ.

In another embodiment, the invention encompasses Form I in the form of the monohydrate.

In another embodiment, the invention provides a process for preparing N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form, wherein the crystalline form is Form I. The process comprises a) providing a mixture comprising (i) N-(4-{4-amino-7-[1-(2-hydroxyethyl)-1H-pyrazol-4-yl]thieno[3,2-c]pyridin-3-yl}phenyl)-N'-(3-fluorophenyl)urea, water, acetone, and citric acid; b) causing N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate crystalline Form I to exist in the mixture. The process can further comprise isolating N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form, wherein the crystalline form is Form I.

The invention further comprises a pharmaceutical composition comprising N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I and one or more pharmaceutically acceptable excipients.

In one embodiment, the invention encompasses N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate in a solid crystalline form.

In another embodiment, the invention encompasses the compound N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate in a solid crystalline form, wherein the crystalline form is Form II, characterized at least by a powder X-ray diffraction peak at any one or more of the following positions: 8.65, 15.18, 24.47, 28.02° 2θ, ±0.2° 2θ.

Another aspect of the invention encompasses a crystalline form of N-(4-{4-amino-7-[1-(2-hydroxyethyl)-1H-pyrazol-4-yl]thieno[3,2-c]pyridin-3-yl}phenyl)-N'-(3-fluorophenyl) urea hydrogen citrate Form II, characterized at least by a powder X-ray diffraction peak at each of the following positions: 8.65, 15.18, 24.47, 28.02° 2θ, ±0.2° 2θ.

Another aspect of the invention encompasses a crystalline form of N-(4-{4-amino-7-[1-(2-hydroxyethyl)-1H-pyrazol-4-yl]thieno[3,2-c]pyridin-3-yl}phenyl)-N'-(3-fluorophenyl) urea hydrogen citrate Form II, characterized at least by a powder X-ray diffraction peak at each of the following positions: 5.71, 6.30, 7.27, 8.65, 9.80, 13.06, 14.31, 15.18, 15.92, 16.68, 17.71, 20.17, 21.98, 23.30, 24.47, 26.11, 28.02° 2θ, ±0.2° 2θ.

In another embodiment, the invention provides a process for preparing N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate in a solid crystalline form, wherein the crystalline form is Form II. The process comprises a) providing a mixture comprising (i) N-(4-{4-amino-7-[1-(2-hydroxyethyl)-1H-pyrazol-4-yl]thieno[3,2-c]pyridin-3-yl}phenyl)-N'-(3-fluorophenyl)urea, water, tetrahydrofuran, and citric acid; and b) causing N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate crystalline Form I to exist in the mixture. The process can further comprise isolating N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate in a solid crystalline form, wherein the crystalline form is Form II.

The invention further comprises a pharmaceutical composition comprising N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate Form II and one or more pharmaceutically acceptable excipients.

The crystalline form of citrate salts of N-(4-{4-amino-7-[1-(2-hydroxyethyl)-1H-pyrazol-4-yl]thieno[3,2-c]pyridin-3-yl}phenyl)-N'-(3-fluorophenyl)urea, for example Form I or II, can be useful as API for the preparation of pharmaceutical compositions suitable for any route of administration, including oral, to a subject in need thereof. Other routes of administration include, without limitation, parenteral, sublingual, buccal, intranasal, pulmonary, topical, transdermal, intradermal, ocular, otic, rectal, vaginal, intragastric, intracranial, intrasynovial and intra-articular routes.

Where it is desired to provide citrate salts of N-(4-{4-amino-7-[1-(2-hydroxyethyl)-1H-pyrazol-4-yl]thieno[3,2-c]pyridin-3-yl}phenyl)-N'-(3-fluorophenyl)urea, for example Form I or II, in solution form, for example in a liquid formulation for oral or parenteral administration, the citrate salts of N-(4-{4-amino-7-[1-(2-hydroxyethyl)-1H-pyrazol-4-yl]thieno[3,2-c]pyridin-3-yl}phenyl)-N'-(3-fluorophenyl)urea will not, of course, be present in such a formulation in crystalline form; indeed, the presence of crystals is generally undesired in such a formulation. However, crystalline N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate or hydrogen citrate of the present invention can nonetheless be important as API in a process for preparing such a formulation.

Even where the desired formulation is one containing N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate or hydrogen citrate in amorphous form, for example a solid dispersion formulation, crystalline N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate or hydrogen citrate can still be useful as API in a process for preparing such a formulation.

As API, a crystalline form of N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate or hydrogen citrate such as Form I or II has advantages over the amorphous form. For example, purification of API to the high degree of purity required by most regulatory authorities is more efficient and therefore costs less where the API is crystalline as opposed to amorphous form. Physical and chemical stability, and therefore shelf-life of the API solid, is also typically better for crystalline than amorphous forms. Ease of handling is improved over the amorphous form, which tends to be oily or sticky. Drying is more straightforward and more easily controlled in the case of the crystalline material, which has a well-defined drying or desolvation temperature, than in the case of the amorphous material, which has greater affinity for organic solvents and no well-defined drying temperature. Downstream processing using crystalline API permits enhanced process control. These advantages are illustrative a non-limiting.

N-(4-{4-amino-7-[1-(2-hydroxyethyl)-1H-pyrazol-4-yl]thieno[3,2-c]pyridin-3-yl}phenyl)-N'-(3-fluorophenyl)urea is present in a pharmaceutical composition of the invention in an amount that can be therapeutically effective when the composition is administered to a subject in need thereof according to an appropriate regimen. Typically, a unit dose (the amount administered at a single time), which can be administered at an appropriate frequency, e.g., twice daily to once weekly, is about 10 to about 1,000 mg, depending on the compound in question. Where frequency of administration is once daily (q.d.), unit dose and daily dose are the same. Illustratively, the unit dose is typically about 25 to about 1,000 mg, more typically about 50 to about 500 mg, for example about 50, about 100, about 150, about 200, about 250, about 300, about 350, about 400, about 450 or about 500 mg.

Excipients include but are not limited to, for example, encapsulating materials and additives such as absorption accelerators, antioxidants, binders, buffers, carriers, coating agents, coloring agents, diluents, disintegrating agents, emulsifiers, extenders, fillers, flavoring agents, glidants, humectants, lubricants, perfumes, preservatives, propellants, releasing agents, sterilizing agents, sweeteners, solubilizers, wetting agents, mixtures thereof and the like.

Excipients for preparation of formulations comprising or made with crystalline N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, copovidone, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, povidone, peanut oil, potassium phosphate salts, potato starch, povidone, propylene glycol, Ringer's solution, safflower oil, sesame oil, silicon dioxide, sodium carboxymethyl cellulose, sodium phosphate salts, sodium lauryl sulfate, sodium sorbitol, sodium stearylfumarate, soybean oil, stearic acids, stearyl fumarate, sucrose, surfactants, talc, tragacanth, tetrahydrofurfuryl alcohol, triglycerides, vitamin E and derivatives thereof, water, mixtures thereof and the like.

Excipients for preparation of compositions comprising or made with N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like.

Excipients for preparation of compositions comprising or made with N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II to be administered osmotically include, for example, chlorofluorohydrocarbons, ethanol, water, mixtures thereof and the like.

Excipients for preparation of compositions comprising or made with N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like.

Excipients for preparation of compositions comprising or made with N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II to be administered rectally or vaginally include, but are not limited to, cocoa butter, polyethylene glycol, wax, mixtures thereof and the like.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the particular compound, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus the daily dose can vary within wide margins, for example from about 10 to about 1,000 mg. Greater or lesser daily doses can be appropriate in specific situations. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses of N-(4-{4-amino-7-[1-(2-hydroxyethyl)-1H-pyrazol-4-yl]thieno[3,2-c]pyridin-3-yl}phenyl)-N'-(3-fluorophenyl)urea are generally about 10 to about 1,000 mg/day, more typically about 50 to about 500 mg/day or about 200 to about 400 mg/day, for example about 50, about 100, about 150, about 200, about 250, about 300, about 350, about 400, about 450 or about 500 mg/day, administered at an average dosage interval of 3 to 10 days, or about 4 to 8 days, or about 7 days.

A composition comprising crystalline N-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II (or prepared using as API) of the invention are suitable for use in monotherapy or in combination therapy, for example with other chemotherapeutics or with ionizing radiation.

A composition comprising crystalline N-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II (or prepared using as API), can be administered in combination therapy with one or more therapeutic agents that include, but are not limited to, alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1 inhibitors), activators of a death receptor pathway, Bcr-Abl kinase inhibitors, BiTE (bi-specific T-cell engager) antibodies, antibody-drug conjugates, biological response modifiers, cyclin-dependent kinase (CDK) inhibitors, cell cycle inhibitors, cyclooxygenase-2 (COX-2) inhibitors, dual variable domain binding proteins (DVDs), human epidermal growth factor receptor 2 (ErbB2 or HER/2neu) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPB), intercalating antibiotics, kinase inhibitors, kinesin inhibitors, JAK2 inhibitors, mammalian target of rapamycin (mTOR) inhibitors, microRNAs, mitogen-activated extracellular signal-regulated kinase (MEK) inhibitors, multivalent binding proteins, non-steroidal anti-inflammatory drugs (NSAIDs), poly-ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids, deltoids, plant alkaloids, small inhibitory ribonucleic acids (siRNAs), topoisomerase inhibitors, ubiquitin ligase inhibitors, and the like.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perform and granzyme B. In this regard, Bcl-2 has been shown to attenuate the induction of apoptosis by both perform and granzyme B. These data suggest that inhibition of Bcl-2 could enhance the cytotoxic effects elicited by T-cells when targeted to cancer cells (Sutton et al. (1997) *J. Immunol.* 158:5783-5790).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263 or ABT-737 in various tumor cell lines (Tse et al. (2008) *Cancer Res.* 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, Cloretazine™ (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include epidermal growth factor receptor (EGFR) inhibitors, endothelial-specific receptor tyrosine kinase (Tie-2) inhibitors, insulin growth factor-2 receptor (IGFR-2) inhibitors, matrix metalloproteinase-2

(MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include Alimta™ (pemetrexed disodium, LY231514, MTA), 5-azacitidine, Xeloda™ (capecitabine), carmofur, Leustat™ (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethenylcytidine, fludarabine, 5-fluorouracil (5-FU) alone or in combination with leucovorin, Gemzar™ (gemcitabine), hydroxyurea, Alkeran™ (melphalan), mercaptopurine, 6-mercaptopurine riboside, methotrexate, mycophenolic acid, nelarabine, nolatrexed, ocfosfate, pelitrexol, pentostatin, raltitrexed, ribavirin, S-1, triapine, trimetrexate, TS-1, tiazofurin, tegafur, vidarabine, UFT and the like.

Antivirals include ritonavir, hydroxychloroquine and the like.

Aurora kinase inhibitors include ABT-348, AZD-1152, MLN-8054, VX-680, aurora A-specific kinase inhibitors, aurora B-specific kinase inhibitors, pan-aurora kinase inhibitors and the like.

Bcl-2 family protein inhibitors other than ABT-263 or compounds of Formula I herein include AT-101 ((−)-gossypol), Genasense™ Bcl-2-targeting antisense oligonucleotide (G3139 or oblimersen), IPI-194, IPI-565, N-(4-(4-((4'-chloro (1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), GX-070 (obatoclax) and the like.

Bcr-Abl kinase inhibitors include dasatinib (BMS-354825), Gleevec™ (imatinib) and the like.

CDK inhibitors include AZD-5438, BMI-1040, BMS-387032, CVT-2584, flavopyridol, GPC-286199, MCS-5A, PD0332991, PHA-690509, seliciclib (CYC-202 or R-roscovitine), ZK-304709 and the like.

COX-2 inhibitors include ABT-963, Arcoxia™ (etoricoxib), Bextra™ (valdecoxib), BMS-347070, Celebrex™ (celecoxib), COX-189 (lumiracoxib), CT-3, Deramaxx™ (deracoxib), JTE-522, 4-methyl-2-(3,4-dimethylphenyl)-1-(4-sulfamoylphenyl)-1H-pyrrole, MK-663 (etoricoxib), NS-398, parecoxib, RS-57067, SC-58125, SD-8381, SVT-2016, S-2474, T-614, Vioxx™ (rofecoxib) and the like.

EGFR inhibitors include ABX-EGF, anti-EGFR immunoliposomes, EGF-vaccine, EMD-7200, Erbitux™ (cetuximab), HR3, IgA antibodies, Iressa™ (gefitinib), Tarceva™ (erlotinib or OSI-774), TP-38, EGFR fusion protein, Tykerb™ (lapatinib) and the like.

ErbB2 receptor inhibitors include CP-724714, CI-1033 (canertinib), Herceptin™ (trastuzumab), Tykerb™ (lapatinib), Omnitarg™ (2C4, petuzumab), TAK-165, GW-572016 (ionafamib), GW-282974, EKB-569, PI-166, dHER2 (HER2 vaccine), APC-8024 (HER2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17AAG, CNF-101, CNF-1010, CNF-2024, 17-DMAG, geldanamycin, IPI-504, KOS-953, Mycograb™ (human recombinant antibody to HSP-90), nab-17AAG, NCS-683664, PU24FCl, PU-3, radicicol, SNX-2112, STA-9090, VER-49009 and the like.

Inhibitors of apoptosis proteins include HGS-1029, GDC-0145, GDC-0152, LCL-161, LBW-242 and the like.

Antibody-drug conjugates include anti-CD22-MC-MMAF, anti-CD22-MC-MMAE, anti-CD22-MCC-DM1, CR-011-vcMMAE, PSMA-ADC, MEDI-547, SGN-19A, SGN-35, SGN-75 and the like.

Activators of death receptor pathway include TRAIL and antibodies or other agents that target TRAIL or death receptors (e.g., DR4 and DR5) such as apomab, conatumumab, ETR2-ST01, GDC0145 (lexatumumab), HGS-1029, LBY-135, PRO-1762, trastuzumab and the like.

Kinesin inhibitors include Eg5 inhibitors such as AZD-4877 and ARRY-520, CENPE inhibitors such as GSK-923295A, and the like.

JAK2 inhibitors include CEP-701 (lesaurtinib), XL019, INCB-018424 and the like.

MEK inhibitors include ARRY-142886, ARRY-438162, PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30 and Torin 1, and the like.

Non-steroidal anti-inflammatory drugs include Amigesic™ (salsalate), Dolobid™ (diflunisal), Motrin™ (ibuprofen), Orudis™ (ketoprofen), Relafen™ (nabumetone), Feldene™ (piroxicam), ibuprofen cream, Aleve™ and Naprosyn™ (naproxen), Voltaren™ (diclofenac), Indocin™ (indomethacin), Clinoril™ (sulindac), Tolectin™ (tolmetin), Lodine™ (etodolac), Toradol™ (ketorolac), Daypro™ (oxaprozin) and the like.

PDGFR inhibitors include CP-673451, CP-868596 and the like.

Platinum chemotherapeutics include cisplatin, Eloxatin™ (oxaliplatin), eptaplatin, lobaplatin, nedaplatin, Paraplatin™ (carboplatin), picoplatin, satraplatin and the like.

Polo-like kinase inhibitors include BI-2536 and the like.

Phosphoinositide-3 kinase inhibitors include wortmannin, LY-294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include Avastin™ (bevacizumab), ABT-869, AEE-788, Angiozyme™ (a ribozyme that inhibits angiogenesis (Ribozyme Pharmaceuticals (Boulder, Colo.) and Chiron (Emeryville, Calif.)), axitinib (AG-13736), AZD-2171, CP-547632, IM-862, Macugen™ (pegaptanib), Nexavar™ (sorafenib, BAY43-9006), pazopanib (GW-786034), vatalanib (PTK-787 or ZK-222584), Sutent™ (sunitinib or SU-11248), VEGF trap, Zactima™ (vandetanib or ZD-6474) and the like.

Antibiotics include intercalating antibiotics such as aclarubicin, actinomycin D, amrubicin, annamycin, Adriamycin™ (doxorubicin), Blenoxane™ (bleomycin), daunorubicin, Caelyx™ and Myocet™ (liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, Valstar™ (valrubicin), zinostatin and the like.

Topoisomerase inhibitors include aclarubicin, 9-aminocamptothecin, amonafide, amsacrine, becatecarin, belotecan, BN-80915, Camptosar™ (irinotecan hydrochloride), camptothecin, Cardioxane™ (dexrazoxane), diflomotecan, edotecarin, Ellence™ and Pharmorubicin™ (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include Avastin™ (bevacizumab), CD40-specific antibodies, chTNT-1/B, denosumab, Erbitux™ (cetuximab), Humax-CD4™ (zanolimumab), IGF1R-specific antibodies, lintuzumab, Panorex™ (edrecolomab), Rencarex™ (WX G250), Rituxan™ (rituximab), ticilimumab, trastuzumab, CD20 antibodies types I and II and the like.

Hormonal therapies include Arimidex™ (anastrozole), Aromasin™ (exemestane), arzoxifene, Casodex™ (bicalutamide), Cetrotide™ (cetrorelix), degarelix, deslorelin, Desopan™ (trilostane), dexamethasone, Drogenil™ (flutamide), Evista™ (raloxifene), Afema™ (fadrozole), Fareston™ (toremifene), Faslodex™ (fulvestrant), Femara™ (letrozole), formestane, glucocorticoids, Hectorol™ (doxercalciferol), Renagel™ (sevelamer carbonate), lasofoxifene, leuprolide acetate, Megace™ (megestrol), Mifeprex™ (mifepristone), Nilandron™ (nilutamide), tamoxifen including Nolvadex™ (tamoxifen citrate), Plenaxis™ (abarelix), prednisone, Propecia™ (finasteride), rilostane, Suprefact™ (buserelin), luteinizing hormone releasing hormone (LHRH) including Trelstar™ (triptorelin), histrelin including Vantas™ (histrelin implant), Modrastane™ (trilostane), Zoladex™ (goserelin) and the like.

Deltoids and retinoids include seocalcitol (EB1089 or CB1093), lexacalcitol (KH1060), fenretinide, Panretin™ (alitretinoin), tretinoin including Atragen™ (liposomal tretinoin), Targretin™ (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include vincristine, vinblastine, vindesine, vinorelbine and the like.

Proteasome inhibitors include Velcade™ (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, Actimmune™ (interferon gamma-1b), interferon gamma-n1, combinations thereof and the like. Other agents include Alfaferone (IFN-α), BAM-002 (oxidized glutathione), Beromun™ (tasonermin), Bexxar™ (tositumomab), Campath™ (alemtuzumab), CTLA4 (cytotoxic lymphocyte antigen 4), dacarbazine, denileukin, epratuzumab, Granocyte™ (lenograstim), lentinan, leukocyte alpha interferon, imiquimod, MDX-010 (anti-CTLA-4), melanoma vaccine, mitumomab, molgramostim, Mylotarg™ (gemtuzumab ozogamicin), Neupogen™ (filgrastim), OncoVAC-CL, Ovarex™ (oregovomab), pemtumomab (Y-muHMFG1), Provenge™ (sipuleucel-T), sargaramostim, sizofiran, teceleukin, Theracys™ (BCG or Bacillus Calmette-Guerin), ubenimex, Virulizin™ (immunotherapeutic, Lorus Pharmaceuticals), Z-100 (Specific Substance of Maruyama or SSM), WF-10 (tetrachlorodecaoxide or TCDO), Proleukin™ (aldesleukin), Zadaxin™ (thymalfasin), Zenapax™ (daclizumab), Zevalin™ (90Y-ibritumomab tiuxetan) and the like.

Biological response modifiers are agents that modify defense mechanisms of living organisms or biological responses, such as survival, growth or differentiation of tissue cells to direct them to have anti-tumor activity, and include krestin, lentinan, sizofiran, picibanil, PF-3512676 (CpG-8954), ubenimex and the like.

Pyrimidine analogs include cytarabine (cytosine arabinoside, ara C or arabinoside C), doxifluridine, Fludara™ (fludarabine), 5-FU (5-fluorouracil), floxuridine, Gemzar™ (gemcitabine), Tomudex™ (raltitrexed), triacetyluridine, Troxatyl™ (troxacitabine) and the like.

Purine analogs include Lanvis™ (thioguanine), Purinethol™ (mercaptopurine) and the like.

Antimitotic agents include batabulin, epothilone D (KOS-862), N-(2-((4-hydroxyphenyl)amino)pyridin-3-yl)-4-methoxybenzenesulfonamide, ixabepilone (BMS-247550), paclitaxel, Taxotere™ (docetaxel), larotaxel (PNU-100940, RPR-109881 or XRP-9881), patupilone, vinflunine, ZK-EPO (synthetic epothilone) and the like.

Ubiquitin ligase inhibitors include MDM2 inhibitors such as nutlins, NEDD8 inhibitors such as MLN4924, and the like.

A composition comprising crystalline N-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II (or prepared using as API) can also be used as radiosensitizers that enhance the efficacy of radiotherapy. Examples of radiotherapy include, but are not limited to, external beam radiotherapy (XBRT), teletherapy, brachytherapy, sealed-source radiotherapy, unsealed-source radiotherapy and the like.

Additionally or alternatively, a composition comprising crystalline N-{4-amino-7-[1-(2-hydroxyethyl)-1H-pyrazol-4-yl]thieno[3,2-c]pyridin-3-yl}phenyl)-N'-(3-fluorophenyl) urea dihydrogen citrate Form I or hydrogen citrate Form II (or prepared using as API) can be administered in combination therapy with one or more antitumor or chemotherapeutic agents selected from Abraxane™ (ABI-007), ABT-100 (farnesyl transferase inhibitor), Advexin™ (Ad5CMV-p53 vaccine or contusugene ladenovec), Altocor™ or Mevacor™ (lovastatin), Ampligen™ (poly(I)-poly(C12U), a synthetic RNA), Aptosyn™ (exisulind), Aredia™ (pamidronic acid), arglabin, L-asparaginase, atamestane (1-methyl-3,17-dione-androsta-1,4-diene), Avage™ (tazarotene), AVE-8062 (combretastatin derivative), BEC2 (mitumomab), cachectin or cachexin (tumor necrosis factor), Canvaxin™ (melanoma vaccine), CeaVac™ (cancer vaccine), Celeuk™ (celmoleukin), histamine including Ceplene™ (histamine dihydrochloride), Cervarix™ (AS04 adjuvant-adsorbed human papilloma virus (HPV) vaccine), CHOP (Cytoxan™ (cyclophosphamide)+Adriamycin™ (doxorubicin)+Oncovin™ (vincristine)+prednisone), combretastatin A4P, Cypat™ (cyproterone), DAB(389)EGF (catalytic and translocation domains of diphtheria toxin fused via a His-Ala linker to human epidermal growth factor), dacarbazine, dactinomycin, Dimericine™ (T4N5 liposome lotion), 5,6-dimethylxanthenone-4-acetic acid (DMXAA), discodermolide, DX-8951f (exatecan mesylate), eniluracil (ethynyluracil), squalamine including Evizon™ (squalamine lactate), enzastaurin, EPO-906 (epothilone B), Gardasil™ (quadrivalent human papilloma virus (Types 6, 11, 16, 18) recombinant vaccine), Gastrimmune™, Genasense™ (oblimersen), GMK (ganglioside conjugate vaccine), GVAX™ (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, Junovan™ and Mepact™ (mifamurtide), lonafarnib, 5,10-methylenetetrahydrofolate, miltefosine (hexadecylphosphocholine), Neovastat™ (AE-941), Neutrexin™ (trimetrexate glucuronate), Nipent™ (pentostatin), Onconase™ (ranpirnase, a ribonuclease enzyme), Oncophage™ (vitespen, melanoma vaccine treatment), OncoVAX™ (IL-2 vaccine), Orathecin™ (rubitecan), Osidem™ (antibody-based cell drug), Ovarex™ MAb (murine monoclonal antibody), paclitaxel albumin-stabilized nanoparticle, paclitaxel, Pandimex™ (aglycone saponins from ginseng comprising 20(S)-protopanaxadiol (aPPD) and 20(S)-protopanaxatriol (aPPT)), panitumumab, Panvac™-VF (investigational cancer vaccine), pegaspargase, peginterferon alfa (PEG interferon A), phenoxodiol, procarbazine, rebimastat, Removab™ (catumaxomab), Revlimid™ (lenalidomide), RSR13 (efaproxiral), Somatuline™ LA (lanreotide), Soriatane™ (acitretin), staurosporine (*Streptomyces staurospores*), talabostat (PT100), Targretin™ (bexarotene), Taxoprexin™ (docosahexaenoic acid (DHA)+paclitaxel), Telcyta™ (canfosfamide, TLK-286), Temodar™ (temozolomide), tesmilifene, tetrandrine, thalidomide, Theratope™ (STn-KLH vaccine), Thymitaq™ (nolatrexed dihydrochloride), TNFerade™ (adenovector: DNA carrier containing the gene for tumor necrosis factor-α), Tracleer™ or Zavesca™ (bosentan), TransMID-107R™ (KSB-311, diphtheria toxins), tretinoin (retin-A), Trisenox™ (arsenic trioxide), Ukrain™ (derivative of alkaloids from the greater celandine plant), Virulizin™, Vitaxin™ (anti-αvβ3 antibody), Xcytrin™ (motexafin gadolinium), Xinlay™ (atrasentan), Xyotax™ (paclitaxel poliglumex), Yondelis™ (trabectedin), ZD-6126 (N-acetylcolchinol-O-phosphate), Zinecard™ (dexrazoxane), zoledronic acid, zorubicin and the like.

In one embodiment, a composition comprising crystalline N-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II (or prepared using as API), is administered in a therapeutically effective amount to a subject in need thereof to treat cancer.

Examples include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myeloeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, In a more particular embodiment, a composition comprising crystalline N-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II (or prepared using as API), is administered in a therapeutically effective amount to a subject in need thereof to treat myelodysplastic syndrome, acute myeloid leukemia, colorectal cancer, non-small cell lung cancer, and ovarian cancer.

In still further embodiments of the invention, there is provided a method for treating cancer in a mammal comprising dissolving N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II in a pharmaceutically acceptable solvent or mixture of solvents, and administering the resulting solution in a therapeutically effective amount to subject having the disease.

In still further embodiments of the invention, there is provided a method for treating cancer in a mammal comprising dispersing N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I or hydrogen citrate Form II in a pharmaceutically acceptable polymeric carrier, and administering the resulting solid dispersion in a therapeutically effective amount to subject having the disease.

EXAMPLES

The following examples are merely illustrative, and do not limit this disclosure in any way.

PXRD data were collected using a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochrometer provided monochromatic radiation. The diffractometer was calibrated using the attenuated direct beam at one-degree intervals. Calibration was checked using a silicon powder line position reference standard (NIST 640c). The instrument was computer controlled using the Symphonix software (Inel Corp., Artenay, France) and the data was analyzed using the Jade software (version 6.5, Materials Data, Inc., Livermore, Calif.). The sample was loaded onto an aluminum sample holder and leveled with a glass slide.

Example 1

Preparation of N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I N-(4-{4-amino-7-[1-(2-hydroxyethyl)-1H-pyrazol-4-yl]thieno[3,2-c]pyridin-3-yl}phenyl)-N'-(3-fluorophenyl)urea free base solids (399.87 mg) was added to 20 mL of acetone:water mixture (75:25 v:v) and heated with stirring at 70° C. for 30 minutes. The sample remained as a suspension. Citric acid (1.2 mL, 1 M) solution in water was added with continued stirring at 70° C. At the end of approximately one hour, the sample was almost completely dissolved. The sample was allowed to cool slowly to ambient temperatures overnight. The suspension was filtered through a 0.22 micron PTFE syringe filter. The filtrate was evaporative cooled by applying vacuum. Amorphous material precipitated forming a milky suspension, which turned into a "gummy" material (sticky mass) after several minutes. The sample was sonicated for approximately thirty minutes, upon which crystallization occurred. The crystalline solid was collected by vacuum filtration.

Example 2

Preparation of N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I N-(4-{4-amino-7-[1-(2-hydroxyethyl)-1H-pyrazol-4-yl]thieno[3,2-c]pyridin-3-yl}phenyl)-N'-(3-fluorophenyl)urea free base solids (398.06 mg) was added to 20 mL of acetone:water mixture (75:25 v:v) and heated with stirring at 70° C. for 30 minutes. The sample remained as a suspension. Citric acid (1.2 mL, 1 M) solution in water was added with continued stirring at 70° C. After adding the citric acid solution, slight more of the solid was observed to dissolve. Within 12 minutes after the addition of citric acid, a suspension was formed. The suspension was stirred at 70° C. for approximately one hour. The solid was isolated by vacuum filtration.

TABLE 1

PXRD Peak Listing: N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate Form I Peak Position (°2 θ)

| |
|---|
| 7.560 |
| 7.959 |
| 11.797 |
| 12.421 |
| 13.435 |
| 14.587 |
| 15.657 |
| 15.953 |
| 16.686 |
| 21.381 |
| 22.396 |
| 22.815 |
| 23.983 |
| 24.504 |
| 24.993 |
| 26.122 |

Example 3

Preparation of N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate Form II N-(4-{4-amino-7-[1-(2-hydroxyethyl)-1H-pyrazol-4-yl]thieno[3,2-c]pyridin-3-yl}phenyl)-N'-(3-fluorophenyl)urea free base solid (102.65 mg) was dissolved in 5 mL of THF/water mixture (80/20 v/v) at 70° C. Citric acid (21.94 mg) was added to the solution followed by the slow addition of heptane (7.5 mL). The appearance of a small amount of precipitant formed in the heptane layer was noted. The precipitant dissolved as it fell into the THF/water layer. The solution was cooled to ambient temperatures. Crystalline solids formed after several days at ambient temperatures. Solid was collected by vacuum filtration.

TABLE 2

PXRD Peak Listing: N-(4-{4-amino-7-[1-(2-hydroxyethyl)-1H-pyrazol-4-yl]thieno[3,2-c]pyridin-3-yl}phenyl)-N'-(3-fluorophenyl)urea hydrogen citrate Form II Peak Position (°2 θ)

| |
|---|
| 5.71 |
| 6.30 |
| 7.27 |
| 8.65 |
| 9.80 |
| 13.06 |
| 14.31 |
| 15.18 |
| 15.92 |
| 16.68 |
| 17.71 |
| 20.17 |
| 21.98 |
| 23.30 |
| 24.47 |
| 26.11 |
| 28.08 |

What is claimed is:

1. The compound N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form, wherein the crystalline form is Form I, characterized at least by a powder X-ray diffraction peak at any one or more of the following positions: 11.80, 14.59, 15.95, 21.38, 26.12° 2θ, ±0.2° 2θ.

2. The compound of claim 1, wherein the crystalline form is Form I, characterized at least by a powder X-ray diffraction peak at each of said positions.

3. The compound of claim 1, wherein the crystalline form is Form I, characterized at least by a powder X-ray diffraction peak at each of said positions: 7.56, 7.96, 11.80, 12.42, 13.44, 14.59, 15.66, 15.95, 16.69, 21.38, 22.40, 22.82, 23.98, 24.50, 24.99, 26.12° 2θ, ±0.2° 2θ.

4. The compound of claim 1, wherein the crystalline form is a monohydrate.

5. A pharmaceutical composition comprising the compound of claim 1 and one or more pharmaceutically acceptable excipients.

6. A process for preparing N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form, wherein the crystalline form is Form I of claim 1, comprising:
  a) providing a mixture comprising (i) N-(4-{4-amino-7-[1-(2-hydroxyethyl)-1H-pyrazol-4-yl]thieno[3,2-c]pyridin-3-yl}phenyl)-N'-(3-fluorophenyl)urea, water, acetone, and citric acid;
  b) causing N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate crystalline Form I to exist in the mixture.

7. The process of claim 6, further comprising isolating N-(4-{4-amino-7-[1-(2-hydroxyethyl)-1H-pyrazol-4-yl]thieno[3,2-c]pyridin-3-yl}phenyl)-N'-(3-fluorophenyl)urea dihydrogen citrate in a solid crystalline form, wherein the crystalline form is Form I.

* * * * *

UNITED STATES PATENT AND TRADEMARK OFFICE
CERTIFICATE OF CORRECTION

| | | |
|---|---|---|
| PATENT NO. | : 8,633,217 B2 | Page 1 of 1 |
| APPLICATION NO. | : 13/155534 | |
| DATED | : January 21, 2014 | |
| INVENTOR(S) | : Zhang et al. | |

It is certified that error appears in the above-identified patent and that said Letters Patent is hereby corrected as shown below:

In the Specification

Column 10, line 11, detailed description: "perform" to read as --perforin--

Column 10, line 13, detailed description: "perform" to read as --perforin--

Signed and Sealed this
Eighth Day of July, 2014

Michelle K. Lee
*Deputy Director of the United States Patent and Trademark Office*